US00PP29525P3

(12) United States Plant Patent
Danziger

(10) Patent No.: US PP29,525 P3
(45) Date of Patent: Jul. 17, 2018

(54) ***GYPSOPHILA* PLANT NAME 'DGYPCOSMIC'**

(50) Latin Name: *Gypsophila paniculata*
Varietal Denomination: DGYPCOSMIC

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 15/330,685

(22) Filed: Oct. 25, 2016

(65) Prior Publication Data

US 2018/0116087 P1 Apr. 26, 2018

(51) Int. Cl.
*A01H 5/02* (2018.01)

(52) U.S. Cl.
USPC ..... Plt./354
CPC ..... *A01H 5/02* (2013.01)

(58) Field of Classification Search
USPC ..... Plt./354
CPC ..... A01H 5/0227; A01H 5/02; A01H 5/00
See application file for complete search history.

(56) References Cited

PUBLICATIONS

Danziger "Dan" Flower Farm 2015 retrieved on Oct. 17, 2017, retrieved from the Internet at http://www.danziger.co.il/files/5037d9dd55a95006ea008423929e5195.pdf 2 pp. (Year: 2015).*
Upov Pluto Plant Variety Database Oct. 17, 2017 for *Gypsophila* retrieved from the Internet at https://www3.wipo.int/pluto/user/en/index.jsp one page (Year: 2017).*

* cited by examiner

*Primary Examiner* — June Hwu
(74) *Attorney, Agent, or Firm* — Cassandra Bright

(57) ABSTRACT

A new and distinct *Gypsophila* cultivar named 'DGYPCOSMIC' is disclosed, characterized by large full, pure white flowers and easy harvest. The new variety is a *Gypsophila*, suitable for cut flower production and outdoor garden or container uses.

2 Drawing Sheets

Latin name of the genus and species: *Gypsophila paniculata.*

Variety denomination: 'DGYPCOSMIC'.

BACKGROUND OF THE INVENTION

The new *Gypsophila* cultivar is a product of a planned breeding program conducted by the inventor, Gavriel Danziger in Moshav Mishmar Hashiva, Israel. The objective of the breeding program was to produce new *Gypsophila* varieties for cut flower production. The open pollination resulting in this new variety was made during the March 2007.

The seed parent is the unpatented, propriety variety referred to as *Gypsophila* 'D-10'. The pollen parent is unknown as it was an open pollination breeding program. The new variety was discovered in December 2007 by the inventor in a group of seedlings resulting from the 2012 open pollination, in a greenhouse in Moshav Mishmar Hashiva, Israel.

Asexual reproduction of the new cultivar 'DGYPCOSMIC' was first performed by basal vegetative cuttings during December 2007, at a greenhouse in Moshav Mishmar Hashiva, Israel. Subsequent propagation has shown that the unique features of this cultivar are stable and reproduced true to type in multiple successive generations.

SUMMARY OF THE INVENTION

The cultivar 'DGYPCOSMIC' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DGYPCOSMIC' These characteristics in combination distinguish 'DGYPCOSMIC' as a new and distinct *Gypsophila* cultivar:

1. Large, full flower
2. Bright, pure white color.
3. Easy to harvest.

PARENT COMPARISON

Plants of the new cultivar 'DGYPCOSMIC' are similar to plants of the seed parent, in most horticultural characteristics, however, plants of the new cultivar 'DGYPCOSMIC' differ in the following;

1. Flower size of the new variety is larger than that of the parent.

COMMERCIAL COMPARISON

Plants of the new cultivar 'DGYPCOSMIC' can be compared to the commercial variety *Gypsophila* 'DGYPXLENCE' unpatented. These varieties are similar in most horticultural characteristics; however, 'DGYPCOSMIC' differs in the following:

1. 'DGYPXLENCE' flowering time is earlier
2. 'DGYPXLENCE' flower is larger in moderate climates.

Plants of the new cultivar 'DGYPCOSMIC' can also be compared to the variety *Gypsophila* 'DGYPBRIDE', unpatented. These varieties are similar in most horticultural characteristics; however, 'DGYPCOSMIC' differs in the following:

1. 'DGYPCOSMIC' flower is larger than the flower of 'DGYPBRIDE'.
2. 'DGYPCOSMIC' flower is fuller in cold and low light conditions.
3. 'DGYPCOSMIC' flower color is more pure white than the flower color of 'DGYPBRIDE'.

BRIEF DESCRIPTION OF THE PHOTOGRAPHS

Figure 1:
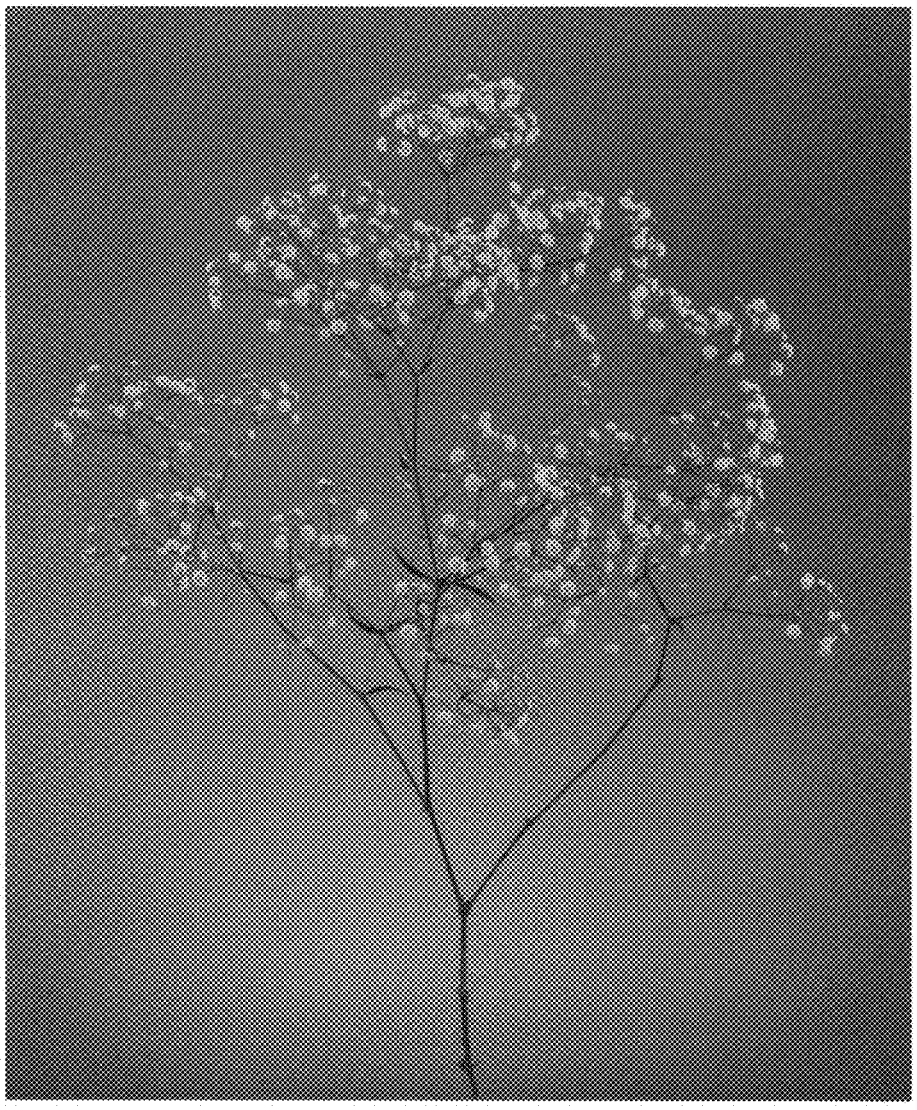

The accompanying photograph in FIG. 1 illustrates in full color multiple inflorescence of 'DGYPCOSMIC' grown outdoors in Moshav Mishmar Hashiva, Israel.

Figure 2:
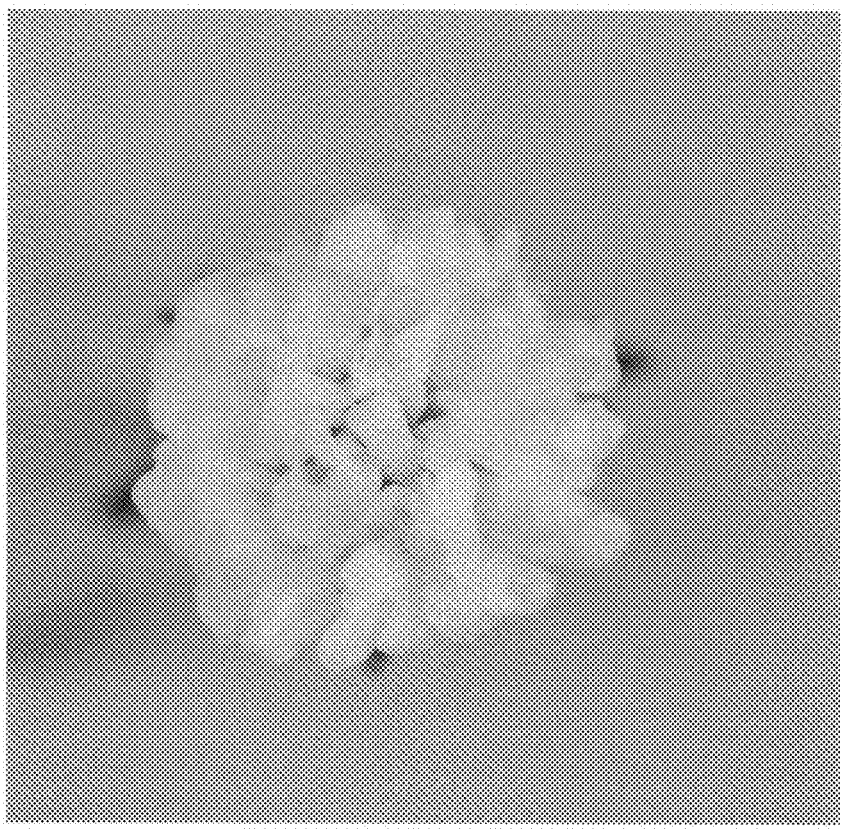

FIG. 2 illustrates in full color a close-up view of a flower of 'DGYPCOSMIC'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DGYPCOSMIC' plants grown in ground beds, outdoors in Moshav Mishmar Hashiva, Israel, under natural lighting. Measurements were taken during April of 2016. The plants were approximately 6 months old. The growing temperature ranged from approximately 12° C. to 35° C. during the days, 4° C. to 28° C. during the nights. Measurements and numerical values represent averages of typical plant types.

Botanical classification: *Gypsophila paniculata* 'DGYPCOSMIC'.

PROPAGATION

Time to initiate rooting: Vegetative cuttings.
Root description: 21 to 28 days at approximately 20° C.
Root description: White Fibers.

PLANT

Growth habit: Upright.
Height: Approximately 90 cm.
Plant spread: Approximately 65 cm.
Growth rate: Approximately 11 weeks in spring-summer Israel conditions.
Branching characteristics: Basal branch and side branches along the main branch.
Length of lateral branches: Approximately 90 cm.
Approximate quantity of lateral branches: Approximately 10.
Diameter of lateral branches: Approximately 0.4 cm.
Texture of lateral branches: Smooth.
Lateral branch shape: Medium upward curvature.
Lateral branch strength: Strong—flexible.
Lateral branch color: Approximately Yellow-Green group, RHS 146-C.
Other stem or plant characteristics: None.
Internode length: 4-6 cm.
Number of leaves per lateral branch: Average 36.
Age of plant described: Approximately 3 month.

FOLIAGE

Leaf:
- *Arrangement*.—Opposite.
- *Compound or single*.—Single. Weak curvature.
- *Shape of blade*.—Acuminate.
- *Average length*.—Approximately 8 cm.
- *Average width*.—Approximately 1.3 cm.
- *Apex*.—Sharply pointed, acuminate to acute.
- *Base*.—Cuneate.
- *Attachment*.—Sessile.
- *Margin*.—Entire.
- *Texture of top surface*.—Rugulose.
- *Texture of bottom surface*.—Rugulose.

Color:
- *Young foliage upper side*.—Near R.H.S. Yellow-Green Group. 147-A.
- *Young foliage under side*.—Near R.H.S. Yellow-Green Group. 147-A.
- *Mature foliage upper side*.—Near R.H.S. Yellow-Green Group. 147-A.
- *Mature foliage under side*.—Near R.H.S. Yellow-Green Group. 147-A.
- *Venation*.—Can be slightly seen.
- *Type*.—Parallel.
- *Venation color upper side*.—Near R.H.S. Yellow-Green Group. 147-A.
- *Venation color under side*.—Near R.H.S. Yellow-Green Group. 147-A.
- *Durability of foliage to stresses*.—As common to *Gypsophila*.

FLOWER

Bloom period:
- *Natural season*.—Spring to Summer.
- *If applicable greenhouse production*.—Approximately 14 weeks.

Inflorescence:
- *Type*.—Thyrse.
- *Height*.—Approximately 90 cm.
- *Width*.—Approximately 65 cm.
- *Quantity of flowers per inflorescence*.—Approximately 900.

Bud:
- *Bud shape*.—Oblate.
- *Bud length*.—Approximately 0.2 cm.
- *Bud diameter*.—Approximately 0.2 cm.
- *Bud color*.—Near R.H.S. Green group 137-B, upper section White Group 155-B.
- *Base/calyx*.—Near R.H.S. Green group 137-B, upper section White Group 155-B.

Individual flower:
- *Shape*.—Rosette. Strongly convex shape from side view.
- *Quantity of flowers and buds per plant*.—Approximately 13,000.
- *Diameter of entire flower*.—Approximately 8 mm.
- *Depth of flower*.—Approximately 5 mm.
- *Rate of opening*.—Individual flowers fully open approximately 4 days from the bud stage.

*Or if cut flower, longevity in vase*.—Approximately 10 days.
*Persistent or self-cleaning*.—Persistent.
*Fragrance*.—Slight to moderate.

Petals:
*Length of petal*.—Approximately 4 mm.
*Width of petal*.—Approximately 1.5 mm.
*Apex*.—Obtuse-truncate, irregularly shallowly notched.
*Shape of petal*.—Obovate.
*Petal margin*.—Entire.
*Petal arrangement*.—Rosette.
*Petal number*.—Approximately 90.
*Petals fused*.—At the very base.
*Petal appearance*.—Matte.
*Petal texture*.—Smooth.

Color:
*Upper surface at first opening*.—Near RHS White Group, 155-C.
*Upper surface at maturity*.—Near RHS White Group, 155-C.
*Upper surface at fading*.—Near RHS White Group, 155-C.
*Under surface at first opening*.—Near RHS White Group, 155-C.
*Under surface at maturity*.—Near RHS White Group, 155-C.
*Under surface at fading*.—Near RHS White Group, 155-B.

Petaloids or other floral structures: No.

Sepal:
*Number*.—5-8.
*Sepal appearance*.—Matte.
*Sepal arrangement*.—2 whorls. (5 at external layer).
*Sepal length*.—Approximately 0.2 cm.
*Sepal width*.—Approximately 0.05 cm.
*Sepal shape*.—Lanceolate.
*Base*.—Acute.
*Apex shape*.—Acuminate to apiculate.
*Margin*.—Entire.
*Color*.—Near R.H.S. Green Group 137-B, transparent margins colored near White Group 155-B.

Peduncle:
*Length*.—Approximately 9.0 cm.
*Diameter*.—Approximately 0.5 cm.
*Angle*.—Approximately 45 degrees.
*Strength*.—Strong, flexible.
*Color*.—Near RHS Yellow-Green Group, 146-C.

Pedicel:
*Length*.—Approximately 0.5 cm.
*Diameter*.—Approximately 0.05 cm.
*Angle*.—Approximately 45 degrees.
*Strength*.—Strong.
*Color*.—Near RHS Yellow-Green Group, 146-A.

REPRODUCTIVE ORGANS

Number of pistils per flower: Not present, or 1 to 2.
Pistil length: Approximately 0.3 cm.
Stigma shape: Not visible.
Stigma color: Near RHS 155-C, White Group.
Style color: Near RHS 155-C, White Group.
Style length: Approximately 0.2 cm.
Ovary color: Near RHS Yellow-Green 144-C upper part has a small blotch Purple N79A.
Stamens quantity: Not observed.

OTHER CHARACTERISTICS

Fruit/seed production: Color and shape of Fruits and Seeds: Kidney shape, Brown Group, N200-A.
Disease/pest resistance: Neither resistance nor susceptibility to normal diseases and pests of *Gypsophila* has been observed.
Drought tolerance: Slightly more tolerance for drought than typical for *Gypsophila*.
Temperature tolerance: USDA zones 3-9.

What is claimed is:

1. A new and distinct cultivar of *Gypsophila* plant named 'DGYPCOSMIC' as herein illustrated and described.

* * * * *